United States Patent [19]

Brand et al.

[11] 4,267,105

[45] May 12, 1981

[54] PROCESS FOR THE RAPID COOLING OF GASES WHICH CONTAIN CAPROLACTAM VAPOR

[75] Inventors: Uwe Brand, Rosengarten; Hugo Fuchs, Ludwigshafen; Ruediger Schmitz, Lambsheim, all of Fed. Rep. of Germany

[73] Assignee: BASF Aktiengesellschaft, Fed. Rep. of Germany

[21] Appl. No.: 138,545

[22] Filed: Apr. 9, 1980

[30] Foreign Application Priority Data

Apr. 23, 1979 [DE] Fed. Rep. of Germany ....... 2916415

[51] Int. Cl.³ .......................................... C07D 201/16
[52] U.S. Cl. ............................................. 260/239.3 A
[58] Field of Search ................................. 260/239.3 A

[56] References Cited

U.S. PATENT DOCUMENTS

| | | | |
|---|---|---|---|
| 3,154,539 | 10/1964 | Irnich | 260/239.3 A |
| 3,210,338 | 10/1965 | Huber et al. | 260/239.3 A |
| 3,350,393 | 10/1967 | Petri et al. | 260/239.3 A |

FOREIGN PATENT DOCUMENTS

| | | | |
|---|---|---|---|
| 920605 | 2/1973 | Canada | 260/239.3 A |
| 2003460 | 8/1971 | Fed. Rep. of Germany | 260/239.3 A |

*Primary Examiner*—Robert T. Bond
*Attorney, Agent, or Firm*—Keil & Witherspoon

[57] ABSTRACT

A process for rapidly cooling gases which contain caprolactam vapor and which have been obtained by catalytic rearrangement of cyclohexanone-oxime in the gas phase in the presence of a supported catalyst containing boric acid, wherein a finely divided coolant at from 90° to 200° C. is fed into a cooling zone from above, gases which are at 330°–400° C. and contain caprolactam vapor are introduced radially at high speed through nozzle orifices over the downstream portion of the cooling zone, and are cooled to 100°–200° C. by thorough mixing with the finely divided coolant, and the cooled mixture is discharged.

6 Claims, No Drawings

PROCESS FOR THE RAPID COOLING OF GASES WHICH CONTAIN CAPROLACTAM VAPOR

The present invention relates to a process for the rapid cooling of gases which contain caprolactam vapor and which have been obtained by catalytic rearrangement of cyclohexanone-oxime in the gas phase, cooling being effected by bringing the gases into contact with a finely divided coolant.

The catalytic rearrangement of cyclohexanone-oxime to caprolactam in the gas phase at from 300° to 400° C. in the presence of a fluidized supported boric acid catalyst gives reaction gases which contain caprolactam vapor. Since caprolactam can decompose at such high temperatures, these gases must be cooled rapidly, for example by chilling with caprolactam or water. Such a process is disclosed, for example, in German Published Application DAS No. 2,003,460. However, it has been found that deposits form at the points at which the caprolactam-containing gas mixture is introduced into the cooling apparatus, and these deposits interfere with the process.

It is an object of the present invention to effect the cooling of gases, containing caprolactam vapor, in such a way that no deposits which can interfere with the process are formed.

We have found that this object is achieved in a process for the rapid cooling of gases which contain caprolactam vapor and which have been obtained by catalytic rearrangement of cyclohexanone-oxime in the gas phase in the presence of a supported catalyst containing boric acid, by chilling the gases by means of a finely divided coolant, wherein a finely divided coolant at from 90° to 200° C. is fed into a cooling zone from above, gases which are at 330°-400° C. and contain caprolactam vapor are introduced radially at high speed through nozzle orifices over the downstream portion of the cooling zone, and are cooled to 100°-200° C. by thorough mixing with the finely divided coolant, and the cooled mixture is discharged.

The novel process has the advantage that it provides a simple method of avoiding the formation of deposits, and thus ensures trouble-free chilling of the hot gases.

Gases containing caprolactam vapor are obtained by catalytic rearrangement of cyclohexanone-oxime in the gas phase in the presence of a supported catalyst containing boric acid. The cyclohexanone-oxime, which may be anhydrous or may contain, for example, up to 10% of water, and which may also contain added boric acid or boron trioxide, is passed, as a vapor, liquid or solid, into the fluidized bed, which contains the catalyst at the reaction temperature. The rearrangement takes place at from 330° to 400° C., preferably from 330° to 370° C. The process may be carried out under atmospheric pressure, reduced pressure or slightly superatmospheric pressure. The catalyst is fluidized by means of an inert gas, such as carbon dioxide, argon or nitrogen, preferably the last-mentioned. Conventional catalysts are used, which contain boron trioxide or boric acid, which under the reaction conditions is converted to boron trioxide, on a carrier. Suitable carriers are, in particular, aluminum oxide in its various modifications, silica, titanium dioxide, mixtures of these oxides with one another, and charcoal. The weight ratio of boron trioxide to carrier is in general from 1:9 to 1:1. Preferred catalysts contain from 25 to 50% by weight of boron trioxide. A suitable process is described, for example, in German Published Application DAS No. 2,003,460. The gases, containing caprolactam vapor, which are thus obtained as a rule contain from 5 to 40% by volume of caprolactam. The remainder consists of inert gases, small amounts of unconverted cyclohexanone-oxime, decomposition products of caprolactam and volatile boric acid compounds originating from the catalyst.

These gases containing caprolactam vapor are chilled by bringing them into contact with a finely divided coolant. For this purpose, finely divided coolant at from 90° to 200° C. is introduced from above into a cooling zone. Examples of suitable coolants are water, molten caprolactam or low-boiling organic solvents, for example hydrocarbons or lower, advantageously water-immiscible, alcohols. The use of molten caprolactam or of water, and particularly of the former, is especially preferred. The temperature at which the coolant is fed in depends on the nature of the coolant employed. Obviously, water is used at from 90° C. to just below the boiling point of water, whilst if caprolactam is used it is advantageous to introduce it at from 150° to 200° C. The fine state of division of the coolant is achieved, for example, by means of single-fluid nozzles. The coolant may be introduced into the top of the cooling zone at one or more points, preferably in such a way that the entire cross-section of the cooling zone is uniformly exposed to finely divided coolant from above.

Over the downstream portion of the cooling zone, gases containing caprolactam vapor, at 330°-400° C., are introduced radially, at high speed, through nozzle orifices. Care must be taken that the gas mixture to be cooled has not already cooled to below 330° C., advantageously not below 350° C., before issuing from the nozzle orifices. The nozzle orifices for introducing the gas may be located on the outside of the cooling zone, so that the gas to be cooled flows radially inward into the cooling zone. Advantageously, the nozzle orifices are arranged over the circumference of the cooling zone and in one plane. It has proved particularly advantageous to feed the gas which is to be cooled coaxially into the cooling zone and introduce it into the said zone in a radial outward direction, in one plane, through a ring-shaped nozzle orifice. Advantageously, the gas velocity at the nozzle orifices is from 10 to 25 m/sec.

As a result of the high flow rate of the gas introduced, and the fine state of division of the coolant, mixing, and hence chilling of the caprolactam to 100°-200° C., occurs very rapidly. The cooling takes place through vaporization of coolant. The amount of coolant used depends on the temperature at which it is introduced and is as a rule from 5 to 60 times the amount of caprolactam to be cooled. If, for example, caprolactam at from 150° to 200° C. is used as the coolant, it has proved advantageous to introduce an amount which is from 5 to 25 times the amount of caprolactam which is to be cooled and is present in the gas mixture.

The cooled mixture, which now consists of inert gas and liquid caprolactam, with or without coolant, is discharged from the cooling zone. Of course the gas mixture contains gaseous caprolactam, with or without coolant, in accordance with the relevant vapor pressure at the temperature employed. The mixture thus obtained is advantageously introduced into the bottom of a column which is cooled with water at the top, in order to achieve complete separation of the caprolactam from the inert gas. Such a procedure is described, for example, in German Published Application DAS No. 2,003,460.

Caprolactam is used for the preparation of polycaprolactam.

The Example which follows illustrates the process according to the invention.

EXAMPLE

About 500 kg of a catalyst consisting of 58% of aluminum oxide and 42% of boron trioxide, and having particles ranging in size from 0.3 to 1.0 mm, are introduced into a reactor having a length of 5,000 mm and a diameter of 1,200 mm. Per hour, 560 kg of nitrogen, which has been brought to 360° C. by electrical heating, are blown through a perforated bottom plate into the reactor, thereby fluidizing the catalyst bed. Per hour, 500 kg of cyclohexanone-oxime containing 4.2% by weight of water are introduced into the fluidized bed through 3 nozzles distributed uniformly over the periphery of the reactor. The temperature at which the nitrogen employed for fluidization is introduced is lowered as the temperature in the reactor tends to rise, so as to maintain a reaction temperature of 360° C. The reaction gases, consisting of caprolactam, water, inert gases and caprolactam decomposition products are next passed through a heated cyclone in order to remove entrained solid particles. From there, the gas mixture, at 360° C., enters the cooling zone. The latter consists of a closed space, into the bottom of which the reaction gases are introduced through a pipe of 200 mm diameter. The upper part of the pipe is provided with a hood, fitted in such a way as to leave an annular gap of about 10 mm between the pipe end and the hood. This feed pipe is jacketed, the jacket being filled with an insulating material so as to minimize the heat transferred to the cooling zone. A single-fluid nozzle, for introducing the caprolactam which serves as the coolant, is mounted centrally above the hood, in the upper part of the cooling zone. About 5,000 kg of caprolactam at 180° C. are passed, per hour, through the nozzle. The chilled gas-liquid mixture escapes through a vapor discharge pipe located in the lower part of the cooling zone and passes into the bottom of a downstream condensation column. Per hour, about 150 liters of water are introduced at the top of this column in order to achieve complete condensation of the lactam. The inert gases, water and low-boiling impurities escape at the top of the column. The amount of lactam corresponding to the amount of lactam formed by rearrangement in the reactor is taken from the column bottom and worked up. In addition, the lactam from the column bottom is used for injection into the cooling zone.

Per hour, about 200 kg of catalyst are taken from the actual reactor, treated with air at about 800° C. in a regenerator, and returned to the reactor. In addition, an amount of solid boric acid corresponding to the losses is added to the catalyst.

Over a period of several weeks, no caked material is detected in the cooling zone.

We claim:

1. A method for rapidly cooling gases which contain caprolactam vapor produced by catalytic rearrangement of cyclohexanone-oxime in the gas phase in the presence of a supported catalyst containing boric acid, in a cooling zone, which comprises;
    (a) feeding a finely divided liquid coolant at a temperature of from 90° to 200° C. into the cooling zone from above;
    (b) injecting the gases containing caprolactam vapor at 330° to 400° C. radially, at high velocity, through nozzle orifices into the cooling zone at locations downstream from the liquid coolant feed;
    (c) mixing thoroughly the gases containing caprolactam vapor with the finely divided liquid coolant to cool said gases to a temperature of from 100° to 200° C.; and
    (d) discharging the cooled mixture of gases and coolant from the cooling zone.

2. A method for rapidly cooling gases which contain caprolactam vapor, as recited in claim 1, wherein the gases which contain caprolactam vapor are injected at a velocity of from 10 to 25 m/sec.

3. A method for rapidly cooling gases which contain caprolactam vapor, as recited in claim 1, wherein said liquid coolant comprises caprolactam at a temperature of from 150° to 200° C.

4. A method for rapidly cooling gases which contain caprolactam vapor, as recited in claim 1, wherein the amount of caprolactam used as coolant is by weight from 5 to 60 times the amount of caprolactam vapor to be cooled.

5. A method for rapidly cooling gases which contain caprolactam vapor, as recited in claim 1, wherein the gases containing caprolactam vapor are injected into the cooling zone in a radially outward direction, in a single plane, through a ring shaped nozzle orifice.

6. A method for rapidly cooling gases which contain caprolactam vapor, as recited in claim 1, wherein the gases containing caprolactam vapor are injected into the cooling zone in a radially inward direction, in a single plane, through orifices arranged around the circumference of the cooling zone.

* * * * *